US00PP23878P3

(12) United States Plant Patent
Danziger

(10) Patent No.: US PP23,878 P3
(45) Date of Patent: Sep. 3, 2013

(54) ***GAILLARDIA* PLANT NAMED 'DGAL3'**

(50) Latin Name: *Gaillardia grandiflora*
Varietal Denomination: DGAL3

(75) Inventor: Gavriel Danziger, Moshav Mishmar Hashiva (IL)

(73) Assignee: Danziger 'Dan' Flower Farm (IL)

( * ) Notice: Subject to any disclaimer, the term of this patent is extended or adjusted under 35 U.S.C. 154(b) by 74 days.

(21) Appl. No.: 13/374,359

(22) Filed: Dec. 23, 2011

(65) Prior Publication Data

US 2013/0167280 P1 Jun. 27, 2013

(51) Int. Cl.
*A01H 5/00* (2006.01)

(52) U.S. Cl.
USPC ..... Plt./431

(58) Field of Classification Search
USPC ..... Plt./431
See application file for complete search history.

*Primary Examiner* — Annette Para
(74) *Attorney, Agent, or Firm* — Cassandra Bright

(57) ABSTRACT

A new and distinct *Gaillardia* cultivar named 'DGAL3' is disclosed, characterized by an intensely colored flower of large size, good branching, somewhat compact plant habit, and abundant flowering. The new variety begins blooming early in the season and flowers over a long period of time. The new variety is a Gaillardia, normally produced as an outdoor garden or container plant.

2 Drawing Sheets

Figure 1:
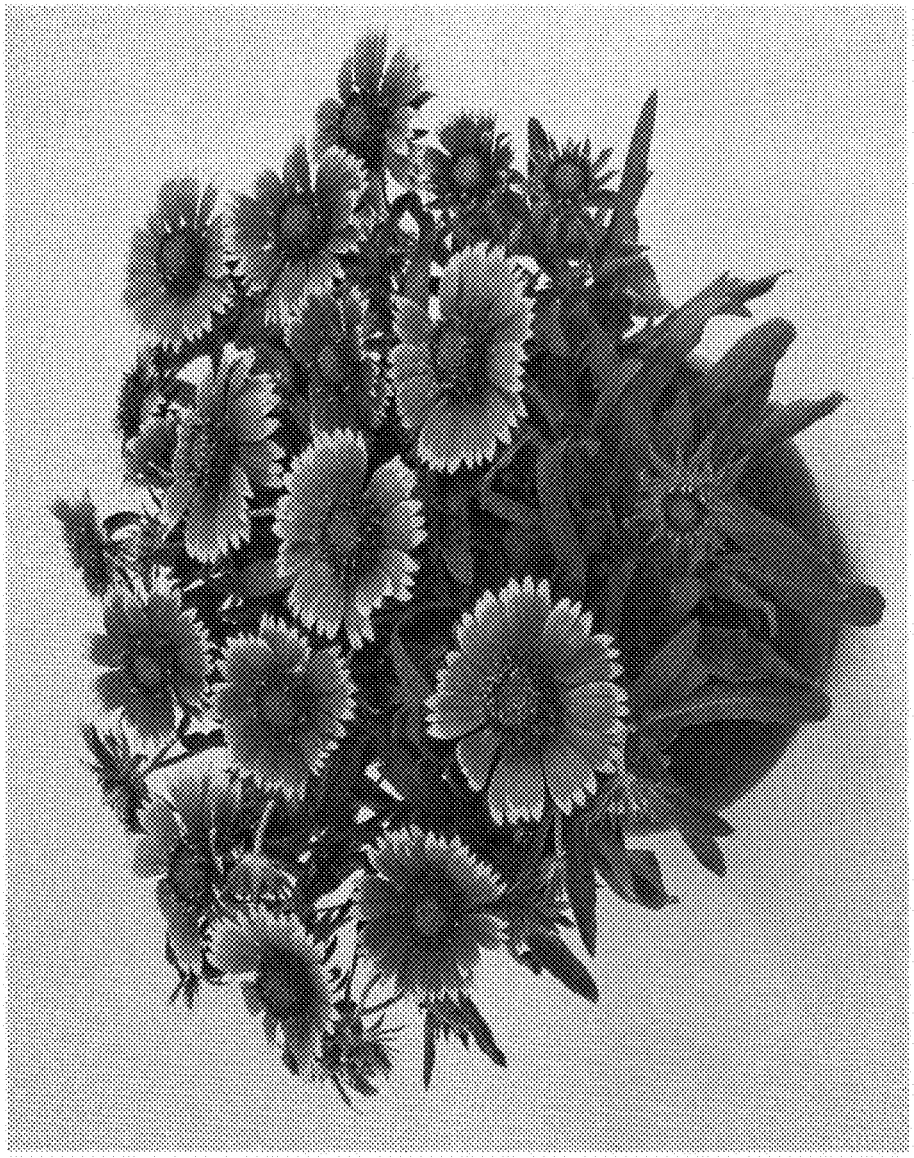

Latin name of the genus and species: *Gaillardia grandiflora.*

Variety denomination: 'DGAL3'.

BACKGROUND OF THE INVENTION

The new *Gaillardia* cultivar is a product of a planned breeding program conducted by the inventor, Gavriel Danziger, in Moshav Mishmar Hashiva, Israel. The objective of the breeding program was to produce new *Gaillardia* varieties for ornamental commercial applications. The cross resulting in this new variety was made during June 2006.

The seed parent is the unpatented, proprietary seedling variety referred to as *Gaillardia grandiflora* 'GAI-3'. The pollen parent is unknown, as the crossing resulting in 'DGAL3' was an open pollination, with unidentifiable pollen parents. The new variety was discovered in April 2007 by the inventor in a group of seedlings resulting from the 2006 crossing, in a research greenhouse in Moshav Mishmar Hashiva, Israel.

Asexual reproduction of the new cultivar 'DGAL3' by vegetative cuttings was first performed at a research greenhouse in Moshav Mishmar Hashiva, Israel in August 2007 and has shown that the unique features of this cultivar are stable and reproduced true to type in successive generations.

SUMMARY OF THE INVENTION

The cultivar 'DGAL3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAL3' These characteristics in combination distinguish 'DGAL3' as a new and distinct *Gaillardia* cultivar:

1. Compact, round habit
2. Abundant flowering
3. Flowering over a long period of time.
4. Well branched plant habit
5. Early blooming
6. Large flower size
7. Intense flowers colors Plants of the new cultivar 'DGAL3' are similar to plants of the seed parent, *Gaillardia grandiflora* 'GAI 3' in most horticultural characteristics, however, plants of the new cultivar 'DGAL3' produce a plant that is more branched, compact in habit and possesses a larger flower size compared to the seed parent. The pollen parent is not known for comparison.

COMMERCIAL COMPARISON

Plants of the new cultivar 'DGAL3' are comparable to the variety *Gaillardia grandiflora* 'Gallo-dark bi-color' U.S. Plant Pat. No. 20,718, but differs in possessing a more compact habit and a deep dark red-purple disk floret color in comparison to red disk floret of the comparison variety.

Plants of the new cultivar 'DGAL3' can also be compared to the commercial variety *Gaillardia grandiflora* 'Gallo-Yellow' U.S. Plant Pat. No. 20,716. Plants of the two varieties are similar in most horticultural characteristics. However plants of 'DGAL3' produce larger flowers, as well as bi-color red and yellow petals color compared to yellow petals of the comparison variety.

BRIEF DESCRIPTION OF THE PHOTOGRAPH

The accompanying photograph in FIG. 1 illustrates in full color a typical plant of 'DGAL3' grown in a greenhouse, in a 12 cm pot. Age of the plant photographed is approximately 8 weeks from a rooted cutting.

Figure 2:
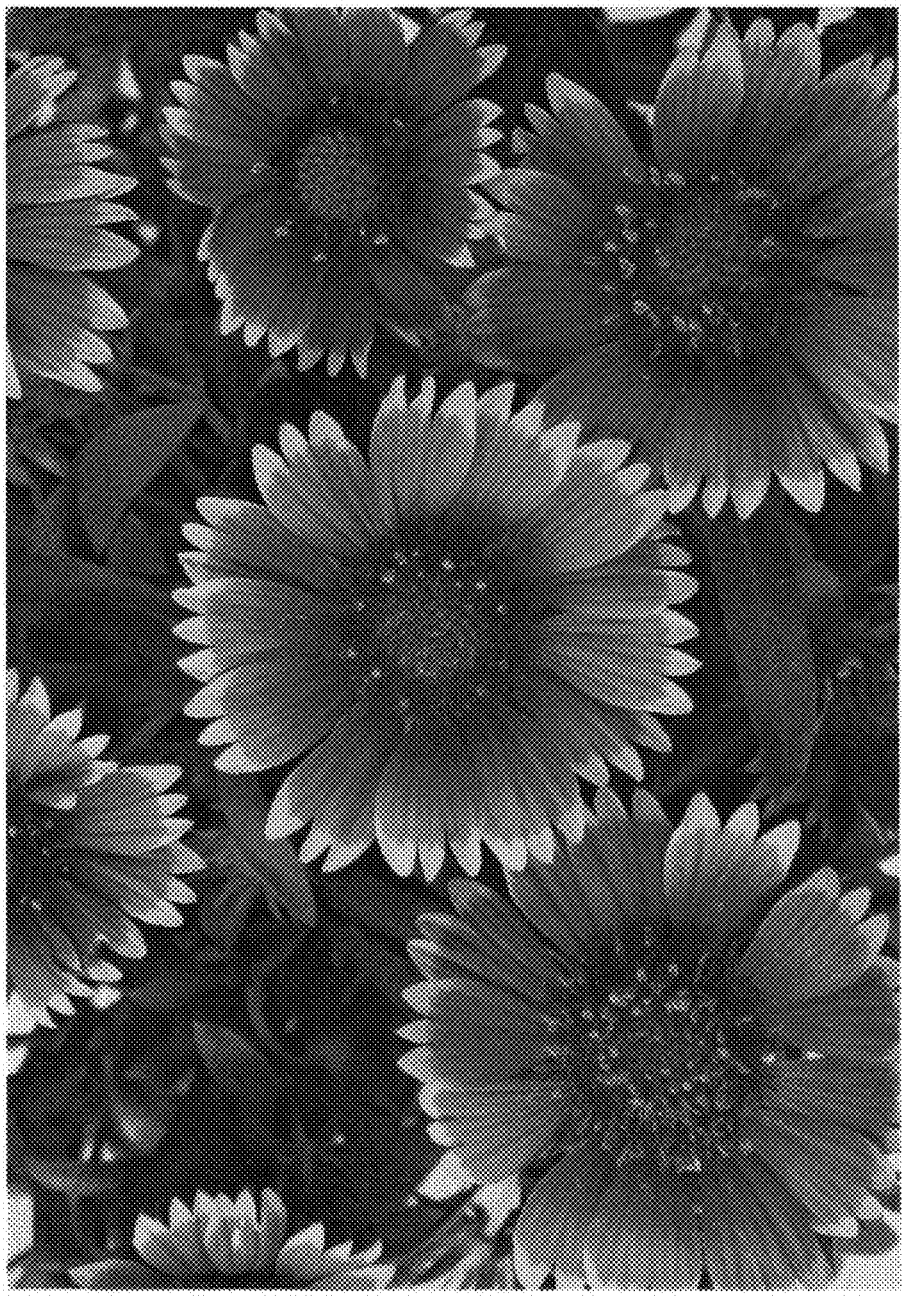

The accompanying photograph in FIG. 2 is a close up of the flowers of the above mentioned plant. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGAL3' plants grown outdoors during May 2011 in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types. Plants are approximately 12 weeks old from a rooted cutting.

Botanical classification: *Gaillardia grandiflora* 'DGAL3'.

PROPAGATION

Time to initiate roots: About 3-4 days at approximately 20° C.
Root description: Fleshy, well branched.

PLANT

Age of plant described: Approximately 84 days from a rooted cutting.
Growth habit: Compact, round and mounded.
Pot size of plant described: 12 cm.
Height: Approximately 20-25 cm.
Plant spread: Approximately 30-35 cm.
Growth rate: As the day gets longer the growth rate changes from moderate to fast.
Branching characteristics: Well Branched.
Length of primary lateral branches: Approximately 8 cm.
Quantity of primary lateral branches: Approximately 5.
Characteristics of primary lateral branches:
- *Diameter*.—0.5-0.7 cm.
- *Color*.—Near RHS Yellow-Green 150D.
- *Texture*.—Lightly covered with thin short soft hairs.
- *Strength*.—Very strong.

Internodes length: Average 1-1.5 cm.

FOLIAGE

Leaf:
- *Shape*.—Oblong.
- *Quantity*.—Approximately 40 per branch.
- *Average length*.—8 cm.
- *Average width*.—1-1.5 cm.
- *Apex*.—Pointed.
- *Base*.—Cordate.
- *Margin*.—Entire.
- *Texture of top surface*.—Slightly smooth.
- *Pubescence*.—Delicate, very light and thin.
- *Aspect*.—30-45 degrees upwards.
- *Color*.—Young foliage upper side: Near RHS Green 137B. Young foliage under side: Near RHS Green 137A. Mature foliage upper side: Near RHS Yellow-Green 147A. Mature foliage under side: Near RHS Yellow-Green 147A.
- *Venation*.—Type: Pinnate. Venation color upper side: Near RHS Yellow-Green 146B. Venation color under side: Near RHS Yellow-Green 147D.
- *Petiole*.—Absent.

FLOWER

Natural flowering season: March-November
Days to flowering from rooted cutting: 4-6 weeks
Inflorescence and flower type and habit: Terminal occurring composite,
Rate of flower opening: 3 to 5 days from bud to fully opened flower.
Flower longevity on plant: 5-7 days
Persistent or self-cleaning: Self cleaning
Flower size:
- *Diameter of entire flower*.—Approximately 8 cm.
- *Depth of flower*.—Approximately 1.5 cm.
- *Disc diameter*.—Approximately cm. 2.5 cm.
- *Quantity of inflorescences per lateral stem*.—3-5.
- *Quantity of open inflorescences and buds per plant*.—30-40.

Bud: (just before opening):
- *Shape*.—Flattened globular.
- *Length*.—1.0 cm.
- *Diameter*.—2 cm.
- *Color*.—Ray florets: Near RHS Yellow group 4B near tip, and Red group 53A near base Disc florets: Near RHS Yellow-Green group 151B at center and Greyed-Purple group 187A at the edge.

Ray florets:
- *Quantity*.—Average 13.
- *Arrangement*.—Rotate in a single whorl.
- *Length*.—3.5 cm.
- *Width*.—1.5 cm.
- *Shape*.—Heart Shaped.
- *Apex*.—Cordate.
- *Base*.—Atteuate.
- *Margin*.—Entire.
- *Texture, upper and lower surfaces*.—Smooth, Slightly ribbed longwise.
- *Color*.—When opening, upper surface: Near RHS Red-Purple group 60A to Red group 46A near center and Yellow-Orange group 14B at the tip. When opening lower surface: Near RHS Yellow-Orange group 14A near tip and Red-Purple 60A at the center. Fully opened, upper surface: Near RHS Yellow-Orange group 14A near tip and Red group 47A at the center. Fully opened, lower surface: Near RHS Yellow-Orange group 14A near tip and Red group 46A at the center.

Disc florets:
- *Quantity*.—150.
- *Arrangement*.—Spirally placed on disc.
- *Length*.—1.2 cm.
- *Width*.—0.5 cm.
- *Shape*.—Tubular.
- *Apex*.—Emarginated.
- *Base*.—Fused.
- *Margin*.—Entire.
- *Texture, upper and lower surfaces*.—Covered with short soft hairs, resulting in velvet texture.
- *Color*.—Mature: Near RHS Red group 49D near base and Red-Purple group 59A at tips. Young: Near RHS Green-Yellow group 1D RHS near center and Purple group N79A Near tip.

Phyllaries/involucral bracts:
*Quantity*.—Approximately 25.
*Length*.—1.5-4 cm (3 spiral rows of involucral bracts, the row near petals are shorter than those that far from petals, range given).
*Width*.—0.3-1.5 cm (3 spiral rows of involucral bracts, the row near petals are narrow than those that far from petals).
*Shape* (*overall*).—Lanceolate Ovate.
*Apex*.—Acute.
*Base*.—Wedge-shaped.
*Texture*.—Dull, Covered with lightsome short thin hairs.
*Margin*.—Entire, with short hair directly on margin.
*Color*.—Near RHS Green 137B.
Peduncles:
*Length*.—Average 6 cm.
*Diameter*.—0.3 cm.
*Angle*.—About 45° to the lateral branch.
*Strength*.—High.
*Texture*.—Slightly glossy due to short and delicate hairs.
*Color*.—Near RHS Yellow-green 147D.
Fragrance: Slightly sweet scent.

REPRODUCTIVE ORGANS

Disc florets:
Stamens:
*Number*.—5.
Anthers:
*Shape*.—Obovate.
*Length*.—Approximately 0.5 mm.
*Color*.—Near RHS Greyed-Purple group N187A.
*Pollen*.—Color: Near RHS Yellow-Orange group 21A. Quantity: Abundant.
Pistil:
*Number*.—One present.
*Length*.—1.4 mm.
*Style*.—Tubular.
*Length*.—5 mm.
*Color*.—Near RHS Yellow group 2D.
*Stigma*.—Shape: Bifid. Color: Near RHS Grayed-Purple group 187A. Ovary Color: Near RHS Yellow group 6D.
Ray florets: No Reproductive Organs Observed on Ray Florets.

OTHER CHARACTERISTICS

Seeds and fruits: 50-70 seeds per flower, Shape — oblong triangle, size — 0.2 cm long×0.15 cm wide, with spiny crown on top 0.3 cm long×0.2 wide.
Disease/pest resistance: Neither resistance nor susceptibility to pathogens and pests common to *Gaillardia* have been observed.
Temperature tolerance: The new variety exhibits a good temperature tolerance range for *Gaillardia*. Known tolerance for high temperatures to at least 35° C. Lower temperature tolerance unknown.

What is claimed is:

1. A new and distinct cultivar of *Gaillardia* plant named 'DGAL3' as herein illustrated and described.

* * * * *